US007276333B1

(12) United States Patent
Masuda et al.

(10) Patent No.: US 7,276,333 B1
(45) Date of Patent: Oct. 2, 2007

(54) VIRAL INFECTION INHIBITOR TARGETING INTEGRASE N-TERMINAL DOMAIN

(75) Inventors: Takao Masuda, Tokyo (JP); Mari Kannagi, Tokyo (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 0 days.

(21) Appl. No.: 09/959,936

(22) PCT Filed: Apr. 25, 2000

(86) PCT No.: PCT/JP00/02698

§ 371 (c)(1),
(2), (4) Date: Nov. 13, 2001

(87) PCT Pub. No.: WO00/70035

PCT Pub. Date: Nov. 23, 2000

(30) Foreign Application Priority Data

May 13, 1999 (JP) ................................ 11/133402

(51) Int. Cl.
*C12Q 1/68* (2006.01)
*C12N 9/00* (2006.01)
*C12N 7/00* (2006.01)
*A61K 48/00* (2006.01)

(52) U.S. Cl. ....................... 435/5; 435/183; 435/235.1; 435/236; 536/23.2; 536/23.72; 424/188.1; 424/208.1; 424/93.2; 514/44

(58) Field of Classification Search ............ 536/24.72, 536/23.2, 23.72; 435/5, 183, 235.1, 236; 424/188.1, 208.1, 93.2; 514/44
See application file for complete search history.

(56) References Cited

FOREIGN PATENT DOCUMENTS

| | | |
|---|---|---|
| EP | 0692032 | 5/1998 |
| JP | 8-505042 | 6/1996 |
| JP | 9-508369 | 8/1997 |
| WO | WO94/06454 | 3/1994 |
| WO | WO94/06454 A1 | 3/1994 |
| WO | WO94/23058 | 3/1994 |
| WO | WO95/19772 | 1/1995 |
| WO | WO98/52970 A1 | 11/1998 |

OTHER PUBLICATIONS

Mazumder et al. Biochemistry 35:13762-13771, 1996.*
Desrosiers (Nature Medicine, Mar. 2004, 10(3): 221-223).*
Leavitt et al (Journal of Biological Chemistry 268:2113-2119, 1993).*

(Continued)

*Primary Examiner*—Bruce R. Campell
*Assistant Examiner*—Stuart W. Snyder
(74) *Attorney, Agent, or Firm*—Venable LLP; Ann S. Hobbs; Robert Kinberg

(57) ABSTRACT

The object of the present invention is to provide a screening method of a new integrase inhibitor being able to inhibit an HIV infection before the reverse transcription step and having a pharmaceutical site of action totally different from those of traditional integrase inhibitors, a new integrase inhibitor being obtainable by the screening method, and pharmaceutical constituents containing the integrase inhibitor and DNA encoding the integrase inhibitor being greatly expected as new remedies for AIDS. A peptide which specifically binds to a peptide at N-terminal domain of retroviral integrase was screened by phage display method, and as a result of the screening, a peptide being able to inhibit the infection and the proliferation of retroviruses such as HIV-1 before the reverse transcription reaction is obtained.

6 Claims, 6 Drawing Sheets

OTHER PUBLICATIONS

Masuda et al (Journal of Virology 69:6687-6696, 1995).*
Cannon et al (Journal of Virology 68:4768-4775, 1994).*
Engelman et al (Journal of Virology 69:2729-2736, 1995).*
Wiskerchen et al (Journal of Virology 69:376-386, 1995).*
Vincent et al (Journal of Virology 67:425-437, 1993).*
Leavitt et al (Journal of Virology 70:721-728, 1996).*
Nakamura et al (Biochemical and Biophysical Research Communications 239:715-722, 1997).*
Leavitt, et al. J Biol Chem (1993) 268:2113-2119.*
Leavitt, et al. J Virol. (1996) 70:721-728.*
Mazumder et al., "Inhibition of the Human Immunodeficiency Virus Type 1 Integrase by Guanosine Quartet Structures", *Biochemistry,* vol. 35, 1996, pp. 13762-13771.
Masuda et al., "Genetic Analysis of Human Immunodeficiency Virus Type 1 Integrase and the U3 *att Site: Unusual Phenotype of Mutants in the Zinc Finger-Like Domain", Journal of Virology,* vol. 69, No. 11, Nov. 1995, pp. 6687-6696.
Katz, et al., "The Retroviral Enzymes" *Annu. Rev. Biochem,* vol. 63, 1994, pp. 133-173.
Engelman et al., "Identificationof Conserved Amino Acid Residues Critical for Human Immunodeficiency Virus Type 1 Integrase Function In Vitro", *Journal of Virology,* vol. 66, No. 11, Nov. 1992, pp. 6361-6369.
Kulkosky et al., "Residues Critical for Retroviral Integrative Recombination in a Region That Is Highly Conserved among Retroviral/Retrotransposon Integrases and Bacterial Insertion Sequence Transposases", *Molecular and Cellular Biology,* vol. 12, No. 5, May 1992, pp. 2331-2338.
LaFemina, et al., "Substrate Specificity of Recombinant Human Immunodeficiency Virus Integrase Protein", *Journal of Virology,* vol. 65, No. 10, Oct. 1991, pp. 5624-5630.
Eijelenboom, et al., "The DNA-binding domain of HIV-1 integrase has an SH3-like fold", *Nature Structural Biology,* vol. 2, No. 9, Sep. 1995, pp. 807-810.
Lodi, et al. "Solution Structure of the DNA Binding Domain of HIV-1 Integrase", *Biochemistry,* vol. 34, 1995, pp. 9826-9833.
Puras et al., "Characterization of the minimal DNA-binding domain of the HIV integrase protein", *Nucleic Acids Research,* vol. 22, No. 20, 1994, pp. 4125-4131.
Zheng, et al. "Zinc folds the N-teminal domain of HIV-1 integrase, promotes multimerization, and enhances catalytic activity", *Proc. Natl. Acad. Sci. USA,* vol. 93, Nov. 1996, pp. 13659-13664.
Cai et al., Solution structure of the N-terminal zinc binding domain of HIV-1 integrase, *Nature Structural Biology,* vol. 4, No. 7, Jul. 1997, pp. 567-577.
Adachi, et al., "Production of Acquired Immunodeficiency Syndrome-Associated Retrovirus in Human and Nonhuman Cells Transfected with an Infectious Molecular Clone", *Journal of Virology,* vol. 59, No. 2, Aug. 1986, pp. 284-291.
Tahei Nakamura et al., "Lack of Infectivity of HIV-1 Integrase Zinc Finger-like Domain Mutant with Morphologically Normal Maturation", Biochemical and Biophysical Research Communication, 1997, pp. 715-722, vol. 239, Academic Press.
Bente M. Nilsen et al., "Monoclonal Antibodies against Human Immunodeficiency Virus Type 1 Integrase: Epitope Mapping and Differential Effects on Integrase Activities In Vitro", Journal of Virology, Mar. 1996, pp. 1580-1587, vol. 70, No. 3, American Society for Microbiology.
Pnina Levy-Mintz et al., "Intracellular Expression of Single-Chain Variable Fragments To Inhibit Early Stages of the Viral Life Cycle by Targeting Human Immunodeficiency Virus Type 1 integrase", Journal of Virology, Dec. 1996, pp. 8821-8832, vol. 70, No. 12, American Society for Microbiology.
Andrew D. Leavitt et al., "Human Immunodeficiency Virus Type 1 Integrase Mutants Retain In Vitro Integrase Activity yet Fail To Integrate Viral DNA Efficiently during Infection", Feb. 1996, pp. 721-728, vol. 70, No. 2, American Society for Microbiology.
Karen A. Vincent, et al., "Characterization of Human Immunodeficiency Virus Type 1 Integrase Expressed in *Escherichia coli*and Analysis of Variants with Amino-Terminal Mutations", Jan. 1993, pp. 425-437, vol. 67, No. 1, American Society for Microbiology.

* cited by examiner

| DB \ AD | WT IN | D64E IN | C43L IN | MA | CA | NC | RT | Vif | Vpr |
|---|---|---|---|---|---|---|---|---|---|
| WT IN | + | +/- | - | - | - | - | - | - | - |
| D64E IN | +/- | +/- | - | - | - | - | - | - | - |
| C43L IN | - | - | - | - | - | - | - | +/- | - |

```
                         SEQUENCE LISTING

<160> NUMBER OF SEQ ID NOS: 23

<210> SEQ ID NO 1
<211> LENGTH: 864
<212> TYPE: DNA
<213> ORGANISM: Human immunodeficiency virus type 1
<220> FEATURE:
<221> NAME/KEY: CDS
<222> LOCATION: (1)..(864)
<223> OTHER INFORMATION: Integrase of Human Immunodeficiency Virus (HIV)
      type 1
<300> PUBLICATION INFORMATION:
<301> AUTHORS: King, P. J.
<302> TITLE: Resistance to the anti-human immunodeficiency virus
      type 1 compound L-chicoric acid results from a single
      mutation at amino acid 140 of integrase
<303> JOURNAL: J. Virol.
<304> VOLUME: 72
<305> ISSUE: 10
<306> PAGES: 8420-8424
<307> DATE: 1998
<308> DATABASE ACCESSION NUMBER: AF078150
<309> DATABASE ENTRY DATE: 1998-09-29
<313> RELEVANT RESIDUES: 1 TO 864

<400> SEQUENCE: 1

ttt tta gat gga ata gat aag gcc caa gaa gaa cat gag aaa tat cac       48
Phe Leu Asp Gly Ile Asp Lys Ala Gln Glu Glu His Glu Lys Tyr His
1               5                   10                  15

agt aat tgg aga gca atg gct agt gat ttt aac cta cca cct gta gta       96
Ser Asn Trp Arg Ala Met Ala Ser Asp Phe Asn Leu Pro Pro Val Val
            20                  25                  30

gca aaa gaa ata gta gcc agc tgt gat aaa tgt cag cta aaa ggg gaa      144
Ala Lys Glu Ile Val Ala Ser Cys Asp Lys Cys Gln Leu Lys Gly Glu
        35                  40                  45

gcc atg cat gga caa gta gac tgt agc cca gga ata tgg cag cta gat      192
Ala Met His Gly Gln Val Asp Cys Ser Pro Gly Ile Trp Gln Leu Asp
    50                  55                  60

tgt aca cat tta gaa gga aaa gtt atc ttg gta gca gtt cat gta gcc      240
```

-continued

```
Cys Thr His Leu Glu Gly Lys Val Ile Leu Val Ala Val His Val Ala
65                  70                  75                  80

agt gga tat ata gaa gca gaa gta att cca gca gag aca ggg caa gaa      288
Ser Gly Tyr Ile Glu Ala Glu Val Ile Pro Ala Glu Thr Gly Gln Glu
                85                  90                  95

aca gca tac ttc ctc tta aaa tta gca gga aga tgg cca gta aaa aca      336
Thr Ala Tyr Phe Leu Leu Lys Leu Ala Gly Arg Trp Pro Val Lys Thr
            100                 105                 110

gta cat aca gac aat ggc agc aat ttc acc agt act aca gtt aag gcc      384
Val His Thr Asp Asn Gly Ser Asn Phe Thr Ser Thr Thr Val Lys Ala
        115                 120                 125

gcc tgt tgg tgg gcg ggg atc aag cag gaa ttt agc att ccc tac aat      432
Ala Cys Trp Trp Ala Gly Ile Lys Gln Glu Phe Ser Ile Pro Tyr Asn
    130                 135                 140

ccc caa agt caa gga gta ata gaa tct atg aat aaa gaa tta aag aaa      480
Pro Gln Ser Gln Gly Val Ile Glu Ser Met Asn Lys Glu Leu Lys Lys
145                 150                 155                 160

att ata gga cag gta aga gat cag gct gaa cat ctt aag aca gca gta      528
Ile Ile Gly Gln Val Arg Asp Gln Ala Glu His Leu Lys Thr Ala Val
                165                 170                 175

caa atg gca gta ttc atc cac aat ttt aaa aga aaa ggg ggg att ggg      576
Gln Met Ala Val Phe Ile His Asn Phe Lys Arg Lys Gly Gly Ile Gly
            180                 185                 190

ggg tac agt gca ggg gaa aga ata gta gac ata ata gca aca gac ata      624
Gly Tyr Ser Ala Gly Glu Arg Ile Val Asp Ile Ile Ala Thr Asp Ile
        195                 200                 205

caa act aaa gaa tta caa aaa caa att aca aaa att caa aat ttt cgg      672
Gln Thr Lys Glu Leu Gln Lys Gln Ile Thr Lys Ile Gln Asn Phe Arg
    210                 215                 220

gtt tat tac agg gac agc aga gat cca gtt tgg aaa gga cca gca aag      720
Val Tyr Tyr Arg Asp Ser Arg Asp Pro Val Trp Lys Gly Pro Ala Lys
225                 230                 235                 240

ctc ctc tgg aaa ggt gaa ggg gca gta gta ata caa gat aat agt gac      768
Leu Leu Trp Lys Gly Glu Gly Ala Val Val Ile Gln Asp Asn Ser Asp
                245                 250                 255

ata aaa gta gtg cca aga aga aaa gca aag atc atc agg gat tat gga      816
Ile Lys Val Val Pro Arg Arg Lys Ala Lys Ile Ile Arg Asp Tyr Gly
            260                 265                 270

aaa cag atg gca ggt gat gat tgt gtg gca agt aga cag gat gag gat      864
Lys Gln Met Ala Gly Asp Asp Cys Val Ala Ser Arg Gln Asp Glu Asp
        275                 280                 285


<210> SEQ ID NO 2
<211> LENGTH: 288
<212> TYPE: PRT
<213> ORGANISM: Human immunodeficiency virus type 1

<400> SEQUENCE: 2

Phe Leu Asp Gly Ile Asp Lys Ala Gln Glu Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
```

-continued

```
                85                  90                  95

Thr Ala Tyr Phe Leu Leu Lys Leu Ala Gly Arg Trp Pro Val Lys Thr
            100                 105                 110

Val His Thr Asp Asn Gly Ser Asn Phe Thr Ser Thr Thr Val Lys Ala
        115                 120                 125

Ala Cys Trp Trp Ala Gly Ile Lys Gln Glu Phe Ser Ile Pro Tyr Asn
    130                 135                 140

Pro Gln Ser Gln Gly Val Ile Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asp Pro Val Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      designed specific binding peptide for amino-terminal
      domain of HIV-1 integrase

<400> SEQUENCE: 3

Ser Ile Leu Pro Tyr Pro Tyr
1               5


<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      designed specific binding peptide for amino-terminal
      domain of HIV-1 integrase

<400> SEQUENCE: 4

Tyr Pro Tyr Tyr Gly Pro Arg
1               5


<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      designed specific binding peptide for amino-terminal
      domain of HIV-1 integrase

<400> SEQUENCE: 5
```

-continued

Thr Asn Ser Glu Arg Ile His
1 5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic designed specific binding peptide for amino-terminal domain of HIV-1 integrase

<400> SEQUENCE: 6

Ser His Val His Pro Arg His Trp His Gln Thr Glu
1 5 10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic designed specific binding peptide for amino-terminal domain of HIV-1 integrase

<400> SEQUENCE: 7

His His His Ala His Pro Ala Pro His Pro Asp Arg
1 5 10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic designed specific binding peptide for amino-terminal domain of HIV-1 integrase

<400> SEQUENCE: 8

Ser His His His Leu Ser Asp His Leu Ser Tyr
1 5 10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic designed specific binding peptide for amino-terminal domain of HIV-1 integrase

<400> SEQUENCE: 9

Cys Gly His Gly His Ser Asn Ser Cys
1 5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic designed specific binding peptide for amino-terminal domain of HIV-1 integrase

<400> SEQUENCE: 10

Cys Asn Ser Ser Lys Met His Thr Cys
1 5

-continued

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic designed specific binding peptide for amino-terminal domain of HIV-1 integrase

<400> SEQUENCE: 11

```
Cys Asn His Gln Ala Leu Pro Arg Cys
1               5
```

<210> SEQ ID NO 12
<211> LENGTH: 55
<212> TYPE: PRT
<213> ORGANISM: Human immunodeficiency virus type 1

<400> SEQUENCE: 12

```
Phe Leu Asp Gly Ile Asp Lys Ala Gln Glu Glu His Glu Lys Tyr His
  1               5                  10                  15

Ser Asn Trp Arg Ala Met Ala Ser Asp Phe Asn Leu Pro Pro Val Val
             20                  25                  30

Ala Lys Glu Ile Val Ala Ser Cys Asp Lys Cys Gln Leu Lys Gly Glu
         35                  40                  45

Ala Met His Gly Gln Val Asp
     50                  55
```

<210> SEQ ID NO 13
<211> LENGTH: 55
<212> TYPE: PRT
<213> ORGANISM: Human immunodeficiency virus type 1

<400> SEQUENCE: 13

```
Phe Leu Glu Lys Ile Glu Pro Ala Gln Glu Glu His Glu Lys Tyr His
  1               5                  10                  15

Ser Asn Val Lys Glu Leu Ser His Lys Phe Gly Ile Pro Asn Leu Val
             20                  25                  30

Ala Arg Gln Ile Val Asn Ser Cys Ala Gln Cys Gln Gln Lys Gly Glu
         35                  40                  45

Ala Ile His Gly Gln Val Asn
     50                  55
```

<210> SEQ ID NO 14
<211> LENGTH: 55
<212> TYPE: PRT
<213> ORGANISM: Human immunodeficiency virus type 1

<400> SEQUENCE: 14

```
Phe Leu Asp Arg Ile Glu Glu Ala Gln Asp Asp His Ala Lys Tyr His
  1               5                  10                  15

Asn Asn Trp Arg Ser Met Val Gln Glu Phe Gly Leu Pro Asn Ile Val
             20                  25                  30

Ala Lys Glu Ile Val Ala Ala Cys Pro Lys Cys Gln Ile Arg Gly Glu
         35                  40                  45

Pro Lys His Gly Gln Val Asp
     50                  55
```

<210> SEQ ID NO 15
<211> LENGTH: 16
<212> TYPE: PRT

-continued

```
<213> ORGANISM: Human immunodeficiency virus type 1

<400> SEQUENCE: 15

Phe Leu Asp Gly Ile Asp Lys Ala Gln Glu Glu His Glu Lys Tyr His
  1               5                  10                  15


<210> SEQ ID NO 16
<211> LENGTH: 14
<212> TYPE: PRT
<213> ORGANISM: Human immunodeficiency virus type 1

<400> SEQUENCE: 16

Phe Asn Leu Pro Pro Val Val Ala Lys Glu Ile Val Ala Ser
  1               5                  10


<210> SEQ ID NO 17
<211> LENGTH: 16
<212> TYPE: PRT
<213> ORGANISM: Human immunodeficiency virus type 1

<400> SEQUENCE: 17

His Glu Lys Tyr His Ser Asn Trp Arg Ala Met Ala Ser Asp Phe Asn
  1               5                  10                  15


<210> SEQ ID NO 18
<211> LENGTH: 13
<212> TYPE: PRT
<213> ORGANISM: Human immunodeficiency virus type 1

<400> SEQUENCE: 18

Cys Gln Leu Lys Gly Glu Ala Met His Gly Gln Val Asp
  1               5                  10


<210> SEQ ID NO 19
<211> LENGTH: 60
<212> TYPE: PRT
<213> ORGANISM: Human immunodeficiency virus type 1

<400> SEQUENCE: 19

Phe Leu Asp Gly Ile Asp Lys Ala Gln Glu Glu His Glu Lys Tyr His
  1               5                  10                  15

Ser Asn Trp Arg Ala Met Ala Ser Asp Phe Asn Leu Pro Pro Val Val
             20                  25                  30

Ala Lys Glu Ile Val Ala Ser Cys Asp Lys Cys Gln Leu Lys Gly Glu
         35                  40                  45

Ala Met His Gly Gln Val Asp Cys Ser Pro Gly Ile
     50                  55                  60


<210> SEQ ID NO 20
<211> LENGTH: 60
<212> TYPE: PRT
<213> ORGANISM: Human immunodeficiency virus type 1

<400> SEQUENCE: 20

Phe Leu Glu Lys Ile Glu Pro Ala Gln Glu Glu His Glu Lys Tyr His
  1               5                  10                  15

Ser Asn Val Lys Glu Leu Ser His Lys Pro Gly Ile Pro Asn Leu Val
             20                  25                  30

Ala Arg Gln Ile Val Asn Ser Cys Ala Gln Cys Gln Gln Lys Gly Glu
         35                  40                  45

Ala Ile His Gly Gln Val Asn Ala Glu Leu Gly Thr
     50                  55                  60
```

-continued

```
<210> SEQ ID NO 21
<211> LENGTH: 60
<212> TYPE: PRT
<213> ORGANISM: Human immunodeficiency virus type 1

<400> SEQUENCE: 21

Phe Leu Asp Arg Ile Glu Glu Ala Gln Asp Asp His Ala Lys Tyr His
  1               5                  10                  15

Asn Asn Trp Arg Ser Met Val Gln Glu Pro Gly Leu Pro Asn Ile Val
             20                  25                  30

Ala Lys Glu Ile Val Ala Ala Cys Pro Lys Cys Gln Ile Arg Gly Glu
         35                  40                  45

Pro Lys His Gly Gln Val Asp Ala Ser Ile Glu Thr
     50                  55                  60


<210> SEQ ID NO 22
<211> LENGTH: 47
<212> TYPE: PRT
<213> ORGANISM: Human immunodeficiency virus type 1

<400> SEQUENCE: 22

Trp Val Asp Arg Ile Glu Glu Ala Glu Ile Asn His Glu Lys Pro His
  1               5                  10                  15

Ser Asp Pro Gln Tyr Leu Arg Thr Glu Phe Asn Leu Pro Lys Met Val
             20                  25                  30

Ala Glu Glu Ile Arg Arg Lys Cys Pro Val Cys Arg Ile Arg Gly
         35                  40                  45


<210> SEQ ID NO 23
<211> LENGTH: 60
<212> TYPE: PRT
<213> ORGANISM: Human immunodeficiency virus type 1

<400> SEQUENCE: 23

Asp Gln Phe Thr Phe Glu Leu Leu Asp Phe Leu His Gln Leu Thr His
  1               5                  10                  15

Leu Ser Phe Ser Lys Met Lys Ala Leu Leu Glu Arg Ser His Ser Pro
             20                  25                  30

Tyr Tyr Met Leu Asn Arg Asp Arg Thr Leu Lys Asn Ile Thr Glu Thr
         35                  40                  45

Cys Lys Ala Cys Ala Gln Val Asn Ala Ser Lys Ser
     50                  55                  60
```

VIRAL INFECTION INHIBITOR TARGETING INTEGRASE N-TERMINAL DOMAIN

TECHNICAL FIELD

The present invention relates to an infection inhibitor against a retrovirus such as an AIDS virus or the like, which can be obtained by targeting N-terminal domain of integrase of a retrovirus such as an AIDS virus or the like, a screening method of the viral inhibitor, and a therapeutic compound or AIDS vaccine containing the viral inhibitor.

PRIOR ART

Human immunodeficiency virus (HIV) which belongs to lentivirus, a kind of retrovirus, is classified into two groups; one is human immunodeficiency virus type-1 (hereinafter "HIV-1") and another is human immunodeficiency virus type-2 (hereinafter "HIV-2"), and it is known that the two groups show 40% homology at gene level. Lentivirus is a pathogenic virus which kills its host cell, and as many other lentiviruses, HIV brings about persistent infection, and shows low activity through most of the infection route. During this process, infectees show almost no symptom and do not notice they are infected, the incubation period lasts 10 years or longer, then finally, almost all of the HIV infectees show the onset of acquired immune deficiency syndrome (AIDS), and meet their death.

It has been known that retroviruses including HIV-1 establish an infection by the following process comprising the steps of; adsorption to targeting cells for the infection, penetration and uncoating, transformation of single stranded RNA genes packaged in viral particles into double stranded DNA by reverse transcriptase, and integration of them to host chromosomes (integration reaction) after nuclear localization. The reverse transcription reaction and the integration reaction in earlier process of a viral infection, which are necessary for the proliferation of HIV-1, are virus-specific reaction processes, it is also known that these reactions are catalyzed by reverse transcriptase (RT), which is a product of polymerase (pol) gene of virus, and by integrase (IN).

As shown in FIG. 1, the integration reaction process of a retrovirus comprises three processes of; ① a 3'-processing reaction in which each terminal of LTR domain on both terminals of viral DNA transformed into DNA by reverse transcriptase is worked on and 2 nucleotides on both 3'-terminals (GT in case of HIV-1) are excised; ② a joining reaction in which viral DNA completing the 3'-processing reaction enters into nucleus and associates with the host chromosome DNA, and each of 5'-terminal phosphoryl groups of the host chromosome DNA, being cut off simultaneously with being nicked by a nucleophilic reaction of both 3'-terminal-OH groups of the viral DNA, and 3'-terminal-OH groups of the viral DNA are ester bound, ③ repair in which each 5'-terminal of the viral DNA and each 3'-terminal of the host chromosome DNA are bound respectively (Annu. Rev. Biochem. 63, 133-173, 1994). It is presumed that the 3'-processing reaction and the joining reaction are reactions directly catalyzed by integrase, and that repair is performed by DNA repair enzyme system of the host cell.

An integrase protein of HIV-1 comprises 288 amino acids in total, and as shown in FIG. 2, has three domains being able to compliment functionally. The three domains are N-terminal domain (peptide containing $1^{st}$ to $50^{th}$ amino acids from N-terminal side), central enzyme activity domain (peptide containing $51^{st}$ to $212^{th}$ amino acids), and C-terminal domain (peptide containing $213^{th}$ to $288^{th}$ amino acids) (In FIG. 2, amino acids conserved in all retrovirus integrase and their positions are shown, and H, C, D and E represent histidine, cystein, aspartic acid and glutamic acid respectively.).

It is said that the enzyme activity domain located at central part of integrase is important for integration reactions, in particular, it has been reported that three amino acid residues of $64^{th}$ and $116^{th}$ aspartic acids and $152^{nd}$ glutamic acid at the enzyme activity domain are essential for an integration reaction involved in binding to $Mg^{2+}$ or $Mn^{2+}$, and that these amino acids are the center of the enzyme activity of integrase (J. Virol. 66, 6361-6369, 1992), (Mol. Cell. Biol. 12, 2331-2338, 1992), (J. Virol. 65, 5624-5630, 1991). In addition, it has been also reported that $136^{th}$, $156^{th}$ and $159^{th}$ lysin residues at this enzyme activity domain and strongly conserved between retroviruses are important for specific binding to viral DNA terminal regions.

C-terminal domain of integrase has DNA binding ability, and the amino acid sequences in this domain show an abundant variety. Its functions including the formation of integrase polymer and nuclear localization are known so far, however, the details are still unknown. Based on a structural analysis by NMR, recently it has been presumed that there is an SH3 (Src-homology 3)-like structure in this C-terminal domain, and that the structure is involved in the formation of dimer of the SH3 or nonspecific DNA binding ability (Nature Structural Biology 2, 807-810, 1995), (Biochemistry 34, 9826-9833, 1995), and as to nonspecific DNA binding ability, the significance of some basic amino acid residues including $264^{th}$ lysin residue has been suggested (Nucleic Acids Research 22, 4125-4131, 1994), (Biochemistry 34, 9826-9833, 1995).

Further, in N-terminal domain of integrase, there is HHCC motif comprised of two histidine residues (H) and two cystein residues (C), which are conserved in integrase of all retroviruses, and because this amino acid motif is similar to Zn finger motif observed in DNA binding domain of some transcriptional regulators, its function was thought to be specific DNA binding region of integrase, however, it is thought to be involved in the formation of dimer or polymer of integrase (Proc. Natl. Acad. Sci. USA. 93, 13659-13664, 1996).

Besides, based on a structural analysis of said N-terminal domain of integrase by NMR, it has been reported that this N-terminal domain has a helix-turn-helix (HTH) structure comprised of four α helix structures shown by α1 to α4 in FIG. 3, that each of two histidine residues and two cystein residues of HHCC motif play an important role for the stabilization of the structure, in other words, the skeletal formation, by being oriented to encompass zinc ions, and that this N-terminal domain forms dimer in liquid (Nature Structural Biology 4, 567-577, 1997). It has been shown that this N-terminal domain is important for the stabilization of dimer formation of integrase molecules, and is involved in integration reactions indirectly, however, its true function is still unknown.

The HTH structure of N-terminal domain is quite similar to the HTH structure represented by a DNA binding region of a tryptophan reppressor protein. As the difference between the HTH structure of N-terminal domain of integrase and the HTH structure represented by a DNA binding region of a tryptophan reppressor protein, it is shown that a domain corresponding to the second helix, which is presumed to be a DNA binding region of a tryptophan repressor protein, is an interface domain between integrase molecules in dimer formation in HIV-1 integrase.

The inventors of the present invention have analyzed HIV-1 mutant stocks to which amino acid substitution mutants of histidine residues or cystein residues which form the skeleton of HHCC motif at integrase N-terminal domain had been introduced, and found that the viral infectivity would be lost almost completely, and reported the fact that the step after the viral adsorption/penetration and before the reverse transcription (uncoating process) would be inhibited as the mechanism of losing infective potency (感染価欠失機字) caused by this point mutation, at the first time in the world (J. Virol. 69, 6687-6696, 1995). Further, on the basis of these studies, now it is presumed that the structure of N-terminal domain having HHCC motif of integrase proteins as its skeleton plays an extremely important role for maintaining the viral infectivity.

Besides, there have been many reports concerning treatment methods for human immunodeficiency virus (HIV). For example, in Published Japanese Translations of PCT International Publication No. 8-503488, there is a description of a treatment method in which patients infected with human immunodeficiency virus (HIV) are injected with polypeptide being subjected to mutation of HIV substrate (MA) polypeptide, which is core protein (Gag polyprotein) of HIV. In Published Japanese Translations of PCT International Publication No. 9-501143, there is a description of biologically active peptide fragments of nef protein of human immunodeficiency virus (HIV), pharmaceutical constituents including these peptides or its biologically active analogues, pharmaceutical constituents including antagonists of peptides and antagonists, and methods for treatment and screening using said compounds and constituents, and in Published Japanese Translations of PCT International Publication No. 10-503654, there is a description of a treatment method in which transdominant negative integrase genes being able to inhibit the replication of retroviruses were used in order to make at least one cell resistant to a retroviral infection.

SUMMARY OF THE INVENTION

For further study of N-terminal domain of integrase, the inventors of the present invention have examined the homology of amino acid sequences of N-terminal domains of integrase among HIV-1, or its relative HIV-2, SIV, heterogeneous retroviruses, and found that there is α-helix-3, a hydrophobic amino acid motif being comprised of hydrophobic amino acid and strongly conserved between species in a domain corresponding to an interface domain in dimer formation of integrase, as shown in FIG. 4 (in FIG. 4, "NL43" indicates N-terminal of integrase gene domain contained in HIV-1 gene, "HIV-$2_{RoD}$" indicates that of integrase gene domain of HIV-2 ROD stock, "$SIV_{AGM}$" indicates that of integrase gene domain of SIV derived from African green monkey, "FIV" indicates that of integrase gene domain of feline immunodeficiency virus, and "MoMuLV" indicates that of integrase domain of murine leukemia virus). Some mutant HIV-1 where amino acid substitutions were introduced to the hydrophobic amino acid motif were constructed and analyzed, and it has been newly found that same as the case of said HIV-1 mutant stocks wherein a substitution mutant has been introduced into each amino acid residue of HHCC, the viral infectivity is lost almost completely at the step before the reverse transcription reaction.

In addition, complete loss of the viral infectivity at the step before the reverse transcription reaction has been also confirmed in HIV-1 mutant stocks wherein four amino acids of HHCC at N-terminal domain of integrase have been respectively substituted with HHCH, HHHC, HHHH, CCHH and CCCC, which are sequences being able to bind to zinc ions, and in HIV-1 mutant stocks to which a substitution mutant of $15^{th}$ tylosin residue, where a phosphorylation reaction is expected, has been introduced.

Based on the analysis of a series of amino acid substitution mutant HIV-1, it has been confirmed that the structure of N-terminal domain of HIV-1 integrase is influenced even by one amino acid substitution and apts to be functionally unstable, resulting in fatal influence on the viral infectivity. Further, the inventors of the present invention have constructed and analyzed substitution mutants of amino acids conserved between species not only for N-terminal domain of HIV-1 integrase, but also for other enzyme activity domain and C-terminal domain, and confirmed that mutants whose viral infectivity is lost almost completely at the step before the reverse transcription reaction are limited to those mutants wherein N-terminal domain of HIV-1 integrase is substituted.

These new findings shown by the inventors provide an extremely helpful suggestion for developing new integrase inhibitors, that is, for developing new remedies and new therapies of AIDS which inhibit the infection of human immunodeficiency virus before the reverse transcription step. Unlike traditional screening methods of integrase inhibitors, which have been focused only on the inhibition of enzyme activity and have been targeting central enzyme activity domain, which is the core of integrase protein, it becomes possible to obtain a new HIV-1 inhibitor having a pharmaceutical site of action totally different from those of traditional inhibitors by targeting N-terminal domain of an integrase protein.

The object of the present invention is to provide a screening method of a new integrase inhibitor being able to inhibit an HIV infection before the reverse transcription step and having a pharmaceutical site of action totally different from those of traditional integrase inhibitors, to provide a new integrase inhibitor being obtainable by the screening method, and to provide a pharmaceutical constituent including the integrase inhibitor and DNA encoding it, which are greatly expected as new remedies for AIDS.

The inventors have given their attention not to the integration step of viral genes, an original field of enzyme activity of integrase proteins, but to N-terminal domain which plays an extremely important role for maintaining the viral infectivity. With integrase mutant clones originally designed and confirmed that they can make viruses lose the infectivity completely, the structure of integrase mutant was analyzed, and it has been found that synthetic peptides having amino acid sequences of the domain where mutation was observed inhibit the replication of HIV-1 with an action different from those of integrase inhibitors reported so far, and thus the present invention has been completed.

The present invention relates to a screening method of a retroviral infection inhibitor characterized in targeting a domain comprised of a whole or a part of N-terminal domain of retroviral integrase or a domain including the N-terminal domain (claim 1), a screening method of a retroviral infection inhibitor characterized in detecting a subject material which binds to a peptide comprised of a whole or a part of N-terminal domain of retroviral integrase or a peptide including the N-terminal domain (claim 2), the screening method of a retroviral infection inhibitor according to claim 2, wherein the binding subject material is a peptide or a protein (claim 3), the screening method of a retroviral infection inhibitor according to claim 3, wherein the peptide or the protein contains an amino acid sequence where one or a few amino acids are deficient, substituted or added in a part of 1st to 55th amino acid sequences among amino acid sequences shown in Seq. ID No. 2 or in a peptide containing said amino acid sequences or a part of said amino acid sequences (claim 4), the screening method of a retroviral infection inhibitor according to claim 3 or 4, wherein the detection of the peptide or the protein is conducted with a method selected from phage display method, immunoprecipitation method, two-hybrid assay and Far Western analysis (claim 5), a screening method of a retroviral infection inhibitor characterized in detecting a subject material which binds to RNA encoding a peptide comprised of a whole or a part of N-terminal domain of retroviral integarase, or a peptide containing the N-terminal domain (claim 6), the screening method of a retroviral infection inhibitor according to claim 6, wherein the binding subject material is DNA or RNA (claim 7), the screening method of a retroviral infection inhibitor according to claim 6, wherein the binding subject material is a peptide or a protein (claim 8), a screening method of a retroviral infection inhibitor characterized in that a wild-type retrovirus is infected to a host cell in the presence of a subject material, and in case the subject material is a peptide, under the condition that DNA encoding the peptide can express, and then the amount of viral gene expression in the host cell after the infection is compared to the case using noninfected control (claim 9), a screening method of a retroviral infection inhibitor characterized in that two-hybrid assay with an integrase gene of a wild-type retrovirus is conducted in the presence of a subject material, and in case the subject material is a peptide, under the condition that DNA encoding the peptide can express, and the inhibition of integrase dimer formation is detected (claim 10), and the screening method of a retroviral infection inhibitor according to any one of claims 1 to 10, wherein the retrovirus is HIV-1 (claim 11).

The present invention also relates to a retroviral infection inhibitor being obtainable by the screening method of a retroviral infection inhibitor according to any one of claims 1 to 11 (claim 12), the retroviral infection inhibitor according to claim 12, wherein the obtainable retroviral infection inhibitor is DNA or RNA (claim 13), the retroviral infection inhibitor according to claim 12, wherein the obtainable retroviral infection inhibitor is a peptide or a protein (claim 14), a retroviral infection inhibitor characterized in comprising a peptide shown in any one of Seq. ID No. 3 to 11, or a peptide or a protein containing said peptide (claim 15), a retroviral infection inhibitor characterized in comprising a peptide having 26th to 39th amino acid sequences among amino acid sequences shown in Seq. ID No. 2, or a peptide or a protein containing said peptide (claim 16), a retroviral infection inhibitor characterized in comprising a monoclonal antibody being obtainable by using a peptide having 1st to 55th amino acid sequences among amino acid sequences shown in Seq. ID No. 2 as an antigen (claim 17), a retroviral infection inhibitor characterized in comprising a complex where the peptide or the protein according to any one of claims 14 to 17 is bound to other peptide or protein, or nonprotein (claim 18), the retroviral infection inhibitor according to claim 18, wherein other peptide or protein, or nonprotein is CD4 glycoprotein, which is T cell antigen (claim 19), the retroviral infection inhibitor according to claim 18, wherein other peptide or protein, or nonprotein is a coat protein of a retrovirus (claim 20), the retroviral infection inhibitor according to any one of claims 18 to 20, wherein the complex is protease-resistant or is chemically modified for intracellular introduction (claim 21), a retroviral infection inhibitor characterized in comprising DNA construct capable of expressing DNA encoding a peptide or a protein, or a part of a protein comprising the retroviral infection inhibitor according to any one of claims 14 to 21 (claim 22), the retroviral infection inhibitor according to claim 22, wherein the DNA construct capable of expression includes a viral vector (claim 23), a retroviral infection inhibitor characterized in comprising DNA which encodes mutant integrase in which one or a few amino acids are deficient, substituted, or added in a peptide comprising a whole or a part of N-terminal domain of retroviral integrase or a peptide including said N-terminal domain, or DNA which hybridizes with said DNA under a stringent condition, wherein the DNA inhibits the replication of retroviruses before the reverse transcription reaction of a retroviral mutant stock containing these DNA (claim 24), the retroviral infection inhibitor according to claim 24, wherein the mutant integrase is selected from some of the amino acid sequences shown in Seq. ID No. 2, which are:

C43H, where 43rd cystein is substituted with histidine;
C40H, where 40th cystein is substituted with histidine;
C40H, C43H, where 40th and 43rd cysteins are substituted with histidines;
H12C, H16C, where 12th and 16th histidines are substituted with cysteins;
H12C, H16C, C40H, C43H, where 12th and 16th histidines are substituted with cysteins, and 40th and 43rd cysteins are substituted with histidines;
P29F, where 29th proline is substituted with phenylalanine;
V32E, where 32nd valine is substituted with glutamic acid;
I36E, where 36th isoleucine is substituted with glutamic acid;
Y15A, where 15th tylosin is substituted with alanine; and
Y15T, where 15th tylosin is substituted with threonine (claim 25), the retroviral infection inhibitor according to any one of claims 12 to 25, wherein the retrovirus is HIV-1 (claim 26).

Further, the present invention relates to a therapeutic constituent characterized in containing the retroviral infection inhibitor according to any one of claims 12 to 26 (claim 27), the therapeutic constituent according to claim 27, wherein the therapeutic constituent containing the retroviral infection inhibitor further contains other antiviral drug (claim 28), the therapeutic constituent according to claim 28, wherein the antiviral drug contains any one of nucleoside or non-nucleoside reverse transcriptase inhibitor, HIV protease inhibitor, and tat inhibitor (claim 29), the therapeutic constituent according to claim 29, wherein the reverse transcriptase inhibitor comprises azidothymidine, dideoxyinosine, dideoxycytosine and d4T (claim 30), the therapeutic constituent according to any one of claims 27 to 30, wherein the retrovirus is HIV-1 (claim 31), a vaccine for a retrovirus characterized in comprising a retrovirus mutant stock having DNA which encodes mutant integrase in which one or a few amino acids are deficient, substituted, or added in a peptide comprising a whole or a part of N-terminal domain of retroviral integrase or a peptide including said N-terminal domain, or DNA which hybridizes with said DNA under a stringent condition, and inhibiting the replication of retroviruses before the reverse transcription reaction of the mutant stock (claim 32), the vaccine for a retrovirus according to claim 32, wherein the mutant integrase is selected from some of the amino acid sequences shown in Seq. ID No. 2, which are:

C43H, where 43rd cystein is substituted with histidine;
C40H, where 40th cystein is substituted with histidine;
C40H, C43H, where 40th and 43rd cysteins are substituted with histidines;

H12C, H16C, where $12^{th}$ and $16^{th}$ histidines are substituted with cysteins;

H12C, H16C, C40H, C43H, where $12^{th}$ and $16^{th}$ histidines are substituted with cysteins, and $40^{th}$ and $43^{rd}$ cysteins are substituted with histidines;

P29F, where $29^{th}$ proline is substituted with phenylalanine;

V32E, where $32^{nd}$ valine is substituted with glutamic acid;

I36E, where $36^{th}$ isoleucine is substituted with glutamic acid;

Y15A, where $15^{th}$ tylosin is substituted with alanine; and Y15T, where $15^{th}$ tylosin is substituted with threonine (claim 33), the vaccine for a retrovirus according to claim 32 or 33, wherein the retrovirus is HIV-1 (claim 34), and a therapy characterized in using the retroviral infection inhibitor according to any one of claims 12 to 26, the therapeutic constituent according to any one of claims 27 to 31, or the vaccine for a retrovirus according to any one of claims 32 to 34 (claim 35).

As the retrovirus of the present invention, any retrovirus can be used as long as it has RNA as a gene, and can convert genomic RNA into DNA with reverse transcriptase. Specific examples are human immunodeficiency virus type 1 (in particular, HIV-1), human immunodeficiency virus type 2 (HIV-2), simian immunodeficiency virus, feline immunodeficiency virus, murine leukemia virus, equine infectious anemia virus, caprine arthritis virus, sheep visna virus, bovine immunodeficiency virus, Mason-Pfizer monkey virus, mouse mammary tumor virus, Rous sarcoma virus, bovine leukemia virus, human T cell leukemia virus, reticuloendotheliosis virus, feline leukemia virus, and human spuma retrovirus. In the present invention, integrase means a protein produced in an infected cell by said retrovirus, and any integrase can be used as long as it can catalyze an integration reaction where viral genome replicated by reverse transcriptase in a host is integrated into a host chromosome.

N-terminal domain of retroviral integrase in the present invention means a domain which binds to a zinc ion or a part of C-terminal side adjacent to the domain in an amino acid sequence of a retroviral integrase protein. For example, in the amino acid sequence of HIV-1 integrase described in Seq. ID No. 2, the domain includes not only N-terminal domain (domain of 1 to 50 amino acid sequences) usually called Zn finger-like domain, but also its adjacent 10 residues or so on C-terminal side. Further, a retroviral infection inhibitor of the present invention means a substance which inhibits a viral infection before the reverse transcription reaction, and the retroviral infection inhibitor of the present invention makes it possible to inhibit the replication and the proliferation of retroviruses.

As the screening method of the retroviral infection inhibitor of the present invention, any method can be used as long as the method targets a domain comprised of a whole or a part of N-terminal domain of retroviral integrase or a domain including the N-terminal domain. For instance, there are detecting methods of subject materials such as peptides or proteins which bind to peptides comprised of a whole or a part of N-terminal domain of retroviral integrase or peptides including the N-terminal domain, which are obtainable through recombinant DNA technology, by utilizing interaction between protein molecules. The examples of such methods include phage display method, immunoprecipitation method, two-hybrid assay and Far Western analysis. Further, peptides or proteins containing amino acid sequences where one or a few amino acids are deficient, substituted or added in a part of amino acid sequences of N-terminal domain of HIV-1 integrase (from $1^{st}$ to $55^{th}$) or in a peptide containing said amino acid sequences or a part of said amino acid sequences are exemplified as possible subject materials of peptides or proteins.

As random oligopeptides, pSKAN system (Mo Bi Tec) can be used in the phage display method, and as for constructing cDNA library, SurfZAP Cloning kit (Stratagene), and phage library (NEB) where random peptides are inserted into phages can be used. For two-hybrid assay, commercial systems including MATCHMAKER (Clontec) or HybridZAP (Stratagene) can be used. In addition, with Far Western analysis, it becomes possible to detect binding proteins as bands on the membrane directly, and to clone them directly when using expression library such as λ gt11 or the like. With these methods, it becomes possible to find new inhibitors with different pharmaceutical sites of action easier than with traditional screening methods where the inhibition of enzyme action is observed.

As subject materials of the present invention, materials which bind to RNA encoding peptides comprised of a whole or a part of N-terminal domain of retroviral integrase or peptides including the N-terminal domain are exemplified other than said materials. DNA or RNA, or, peptides or proteins are examples of the materials which bind to viral RNA, and it is possible to confirm regions in base sequences of viral RNA to which proteins are specifically bound, for instance, by foot printing analysis using ribonuclease.

Examples of the screening methods of the present invention include a method wherein a wild-type retrovirus is infected to a host cell in the presence of a subject material, and in case the subject material is a peptide, under the condition that DNA encoding the peptide can express and then the amount of viral gene expression in the host cell after the infection is compared to the case using noninfected control (Mock), and a method wherein two-hybrid assay with an integrase gene of a wild-type retrovirus is conducted in the presence of a subject material, and in case the subject material is a peptide, under the condition that DNA encoding the peptide can express and the inhibition of integrase dimer formation is detected.

As retroviral infection inhibitors of the present invention, substances obtainable by said screening methods of retroviral infection inhibitors, for example, DNA or RNA, or, peptides or proteins; nine peptides described in Seq. ID No. 3 to 11, revealed by phage display method targeting recombinant purified proteins in integrase N-terminal domain that they are bound to said recombinant purified proteins, or peptides or proteins including said peptides; peptides having $26^{th}$ to $39^{th}$ amino acid sequences among amino acid sequences described in Seq. ID No. 2, which are peptides in the vicinity to α3 in N-terminal domain of HIV-1 integrase, or peptides or proteins including said peptides are exemplified. Further, monoclonal antibodies specifically recognizing N-terminal domain of retroviral integrase are exemplified as retroviral infection inhibitors.

In addition, as retroviral infection inhibitors of the present invention, a complex where said peptides or proteins having retroviral infection inhibiting activity are bound to other peptides or nonproteins including proteins or glycoproteins can be exemplified. Specific examples of said complex are complexes to which CD4 glycoproteins, which are T cell antigens, or coat proteins of retroviruses are bound, and it is preferable to use complexes being modified to be protease-resistant or have improved permeability to cells by chemical modification or the like.

Besides, it is possible to make proteins or the like which comprise said retroviral infection inhibitor present in cells by expressing them in the cells. In other words, as DNA encoding peptides or proteins, or a part of protein, it is possible to use DNA construct being able to express said DNA, for example, DNA construct in which said DNA is incorporated into a viral vector or the like so that the DNA would be able to express.

Other than the above-mentioned inhibitors, an example of the retroviral infection inhibitors of the present invention is a transdominant negative integrase gene lacking its activity which can inhibit the replication of retroviruses, for example, a gene comprising DNA which encodes mutant integrase in which one or a few amino acids are deficient, substituted, or added in a peptide comprising a whole or a part of N-terminal domain of retroviral integrase or a peptide including said N-terminal domain, or DNA which hybridizes with said DNA under a stringent condition, that inhibits the replication of retroviruses before the reverse transcription reaction of a retroviral mutant stock containing these DNA.

Specific examples of the inactivated mutant integrase genes are mutant integrase genes selected from some of the amino acid sequences of wild-type HIV-1 integrase described in Seq. ID No. 2, which are; (C43H), where $43^{rd}$ cystein is substituted with histidine; (C40H), where $40^{th}$ cystein is substituted with histidine; (C40H, C43H), where $40^{th}$ and $43^{rd}$ cysteins are substituted with histidines; (H12C, H16C), where $12^{th}$ and $16^{th}$ histidines are substituted with cysteins; (H12C, H16C, C40H, C43H), where $12^{th}$ and $16^{th}$ histidines are substituted with cysteins and $40^{th}$ and $43^{rd}$ cysteins are substituted with histidines; (P29F), where $29^{th}$ proline is substituted with phenylalanine; (V32E), where $32^{nd}$ valine is substituted with glutamic acid; (I36E), where $36^{th}$ isoleucine is substituted with glutamic acid; (Y15A), where $15^{th}$ tylosin is substituted with alanine; (Y15T), where $15^{th}$ tylosin is substituted with threonine, or the like.

As the therapeutic constituents of the present invention, constituents containing said retroviral infection inhibitors are exemplified, and the constituents include antiviral drugs such as a tat inhibitor, an HIV protease inhibitor, and nucleoside or non-nucleoside reverse transferase inhibitors comprising azidothymidine, dideoxyinosine, dideoxycytosine, d4T and the like. The therapeutic constituents of the present invention are useful as remedies for AIDS.

Further, examples of AIDS vaccines or other such vaccines for retroviruses of the present invention include vaccines comprised of retroviral mutant stocks having DNA which encodes mutant integrase in which one or a few amino acids are deficient, substituted, or added in a peptide comprising a whole or a part of N-terminal domain of retroviral integrase or a peptide including said N-terminal domain, or DNA which hybridizes with said DNA under a stringent condition, that inhibits the replication of retroviruses before the reverse transcription reaction of the mutant stock. Specifically, vaccines comprising mutant stocks which have mutant integrase genes selected from said (C43H), (C40H), (C40H, C43H), (H12C, H16C), (H12C, H16C, C40H, C43H), (P29F), (V32E), (I36E), (Y15A), (15T) and the like, are exemplified.

Said retroviral infection inhibitors, therapeutic constituents or vaccines for retroviruses can be used in the therapies in the present invention.

BEST MODE FOR CARRYING OUT THE INVENTION

The present invention will now be explained in detail with examples, but the technical scope of the present invention is not limited to those examples.

EXAMPLE 1

Generation of Mutant Clones of HIV-1 Integrase

Figure 4:
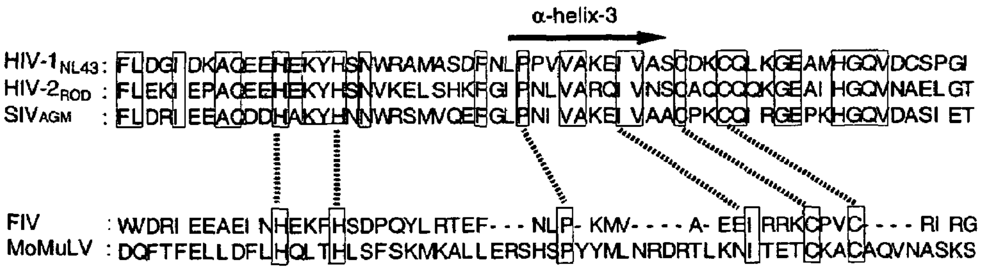
FIG. 4 is a view showing amino acid residues conserved in N-terminal domain of retroviral integrase being targeted (SEQ ID NOS 19-23 are disclosed respectively, in order of appearance).

Mutagenetic DNA fragment of HIV-1 integrase was obtained from pNL4-3, which is an infectious clone, by the method previously described (J. Virol. 59, 284-291, 1986). As mutagenetic DNA fragment of HIV-1 integrase, 4.3 kb fragment covering from SPeI site to SalI site of the pNL4-3 was subcloned into pBluescript SK (Stratagene). This vector DNA was prepared to be single-stranded DNA, and the single-stranded DNA was subjected to site-directed mutagenesis with helper phage M13K07 according to the instructions in the protocol of T7-GEN in vitro mutagenesis kit (Biochemical, U.S.A.), and mutant clones of HIV-1 integrase such as said (C43H), (C40H), (C40H, C43H), (H12C, H16C), (H12C, H16C, C40H, C43H), (P29F), (V32E), (I36E), (Y15A), (15T) and the like were obtained (see FIG. 4).

EXAMPLE 2

Figure 5:
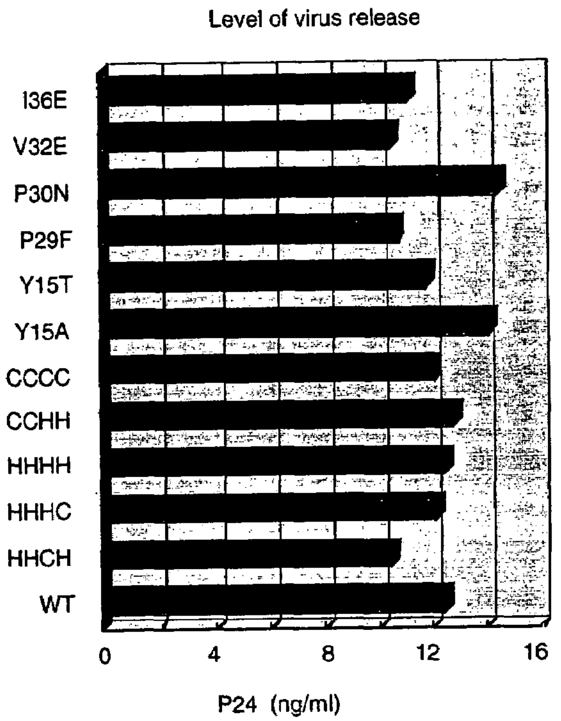
FIG. 5 is a view showing the release of viral particles after cell infections in HIV-1 integrase mutant clones.

Generation of a Pseudotype Virus from Each HHCC Motif Mutant Clone and Amphotropic Envelope of Murine Leukemia Virus 1 μg mutant clones of HIV-1 integrase (pNLlucΔBgIII) obtained by the method described in Example 1, and 1 μg amphotropic envelope expression vector of murine leukemia virus (pDJ-1) were mixed in 10 μl Lipofect amine (BRL), then brought into reaction for 30 minutes at 30° C. The reactant was added to COS cells and transfected. Six hours after the transfection, 4 ml DMEM (Dulbecco's modified Eagle's medium) supplemented with 10% of bovine serum was added and then cultivation was conducted. 24 hours later, the culture liquid was replaced by 4 ml new culture liquid of the same type, and the cultivation was continued to generate pseudotype viruses released from COS cells to culture liquid, and the amount of viral particle release in the viruses was determined by p24 solid phase enzyme immunoassay (FIG. 5). The obtained culture liquid was used as viral solution, and for control, COS cell culture liquid where no plasmid was transfected was used as non-viral solution (Mock) in the following experiments.

Figure 6:
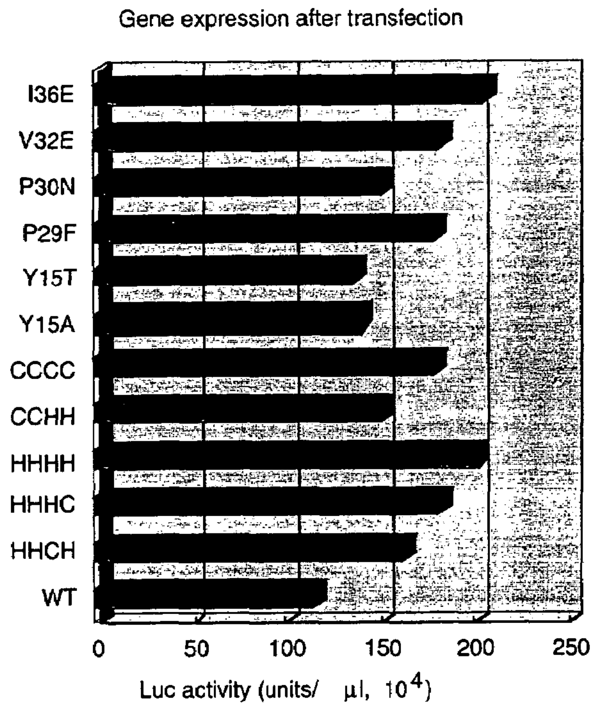
FIG. 6 is a view showing the amount of viral gene expression after COS cell infections in HIV-1 integrase mutant clones.

By examining the amount of provirus gene expression, the influence of mutant clones of each virus on the generation of said pseudotype viruses was investigated. Six hours after the above-stated transfection, all COS cells were washed in PBS (phosphate buffered saline) three times, and the COS cells were added with 200 μl 1×luciferase solution (Promega) and dissolved, then with luminometer Monolight 2010 (Analitical luminescence laboratory, San Diego, Calif.), 10 μl of the solution was subjected to luciferase assay, and the amount of provirus expression was measured (FIG. 6). Collectively, it was shown that mutant clones of each virus did not influence on the expression of provirus genes and the release of viral particles.

EXAMPLE 3

Infectivity of Each Mutant Virus

Figure 7:
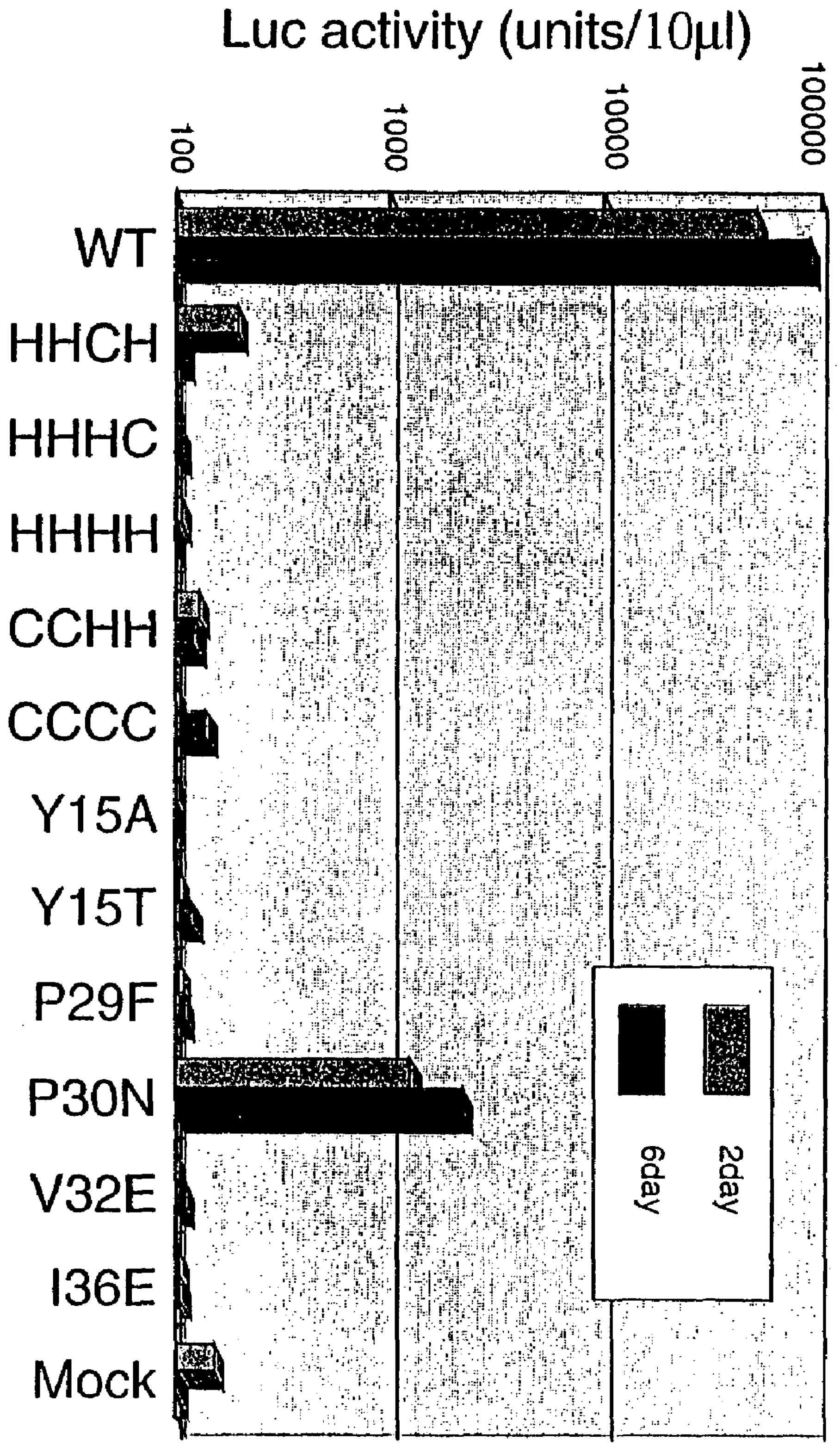
FIG. 7 is a view showing the amount of viral gene expression after RD cell infections in HIV-1 integrase mutant clones.

About 50 ng of each viral solution determined by p24 solid phase enzyme immunoassay described in Example 2 was added with deoxyribonuclease I and treated for 30 minutes in the presence of 10 mM magnesium chloride. The viral infection was conducted by inoculating the obtained DNA of each mutant virus to RD cells (human rhabdomyosarcoma cells). Two days and six days after the infection, virus genes emerging in the infected cells were measured by said luciferase assay (FIG. 7). As a result, all mutant viruses excluding one example (the mutant virus of P30N) showed smaller values than Mock, indicating that the viral infectivity is severely inhibited by the viral mutation.

EXAMPLE 4

Figure 8:
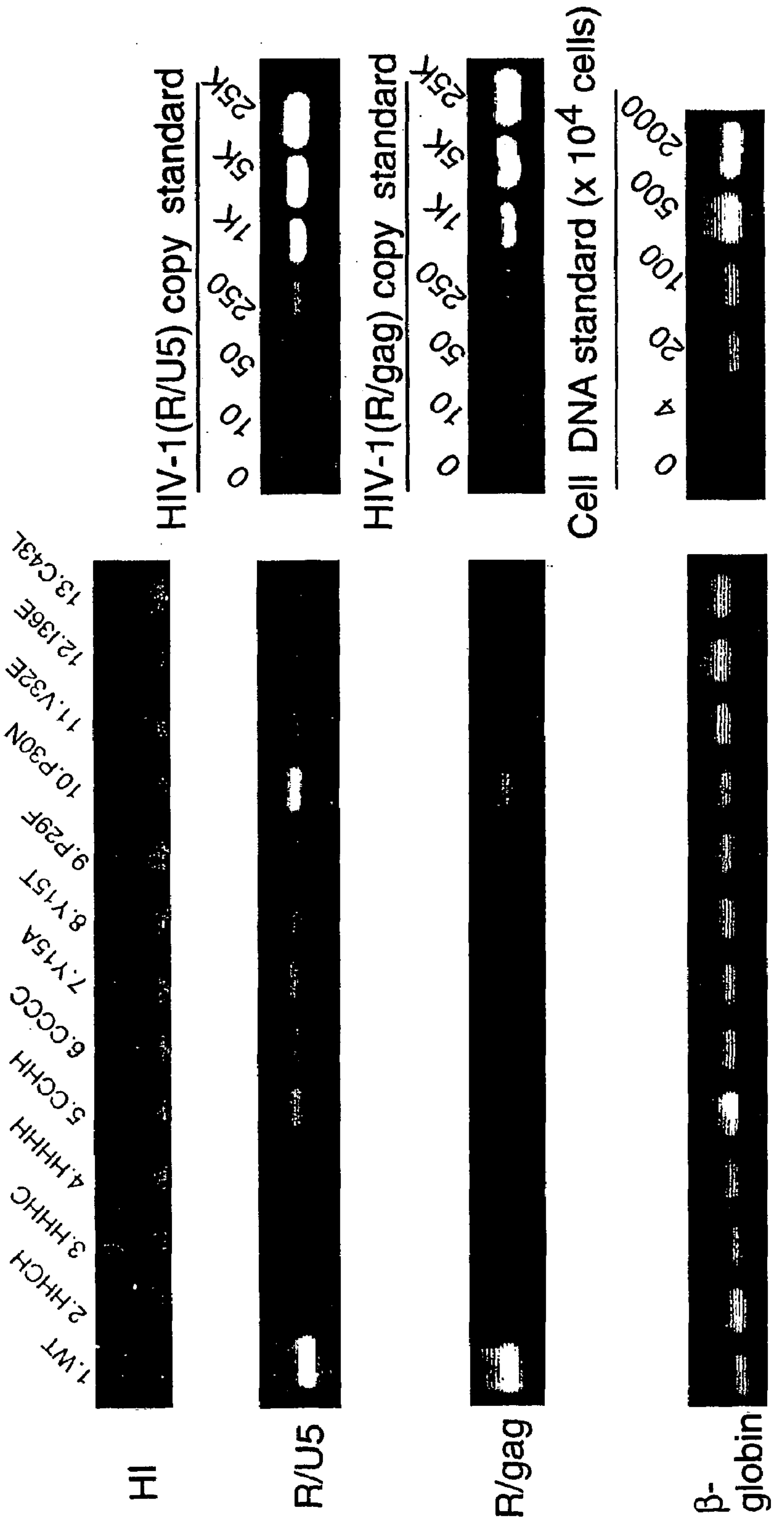
FIG. 8 is a view showing that the infection was inhibited before the reverse transcription in HIV-1 integrase mutant clones.

Confirmation of Severe Inhibition of Infectivity by Each Mutant Virus Before the Reverse Transcription Reaction Whether the viral infectivity was completely lost before the reverse transcription reaction in each of these mutant viruses was confirmed by the following method. Whole DNA was extracted from RD cells two days after the viral infection described in Example 3 by urea lysis method. The extract liquid containing DNA was treated with phenol and chloroform, then subjected to ethanol precipitation to purify DNA, and subsequently added to 100 μl ultra pure water to be redissolved. Viral genes contained in the DNA solution were amplified by PCR with HIV-1-specific primers (R/U5, R/gag) (the amplification was conducted by 30 cycles; one cycle comprises heat-denaturation at 94° C. for 1 minute, annealing at 55° C. for 2 minutes, and synthetic reaction at 72° C. for 2 minutes). The resulted PCR product was fractionated by 2% agarose gel electrophoresis, then stained by cyber green and visualized (FIG. 8). As a result, no viral DNA was detected in all mutant viruses excluding one example (the mutant virus of P30N) even with R/U5 and R/gag as primers, indicating that the viral infectivity is severely inhibited before the reverse transcription reaction.

EXAMPLE 5

Yeast Two-Hybrid Assay

Figures 9, 10:
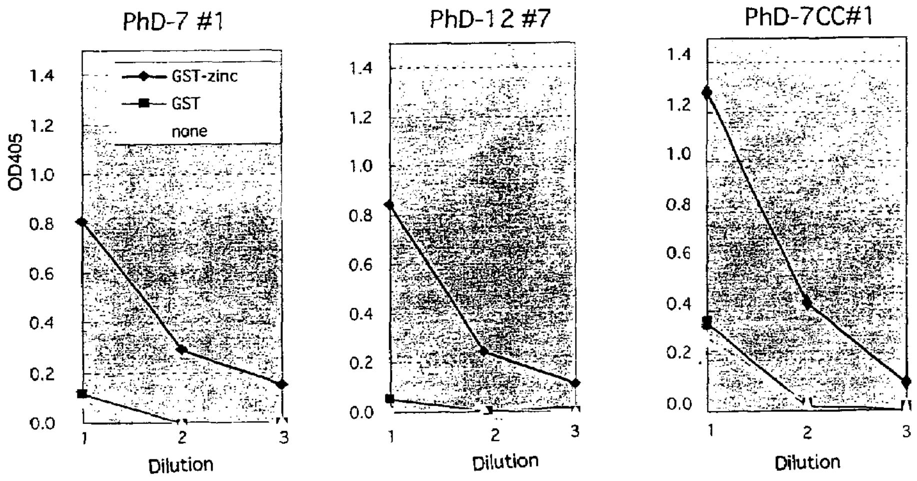
FIG. 9 is a view showing the protein interaction of HIV-1 integrase mutant clones upon two-hybrid assay.
FIG. 10 is a view showing the specific binding of viral infection inhibitors upon phage display method.

As to wild-type HIV-1 integrase and its mutant, dimer formation ability and protein interaction in association with other viral structural proteins were examined with Gal-4 yeast two-hybrid system, and the results are shown in FIG. 9. WTIN, D64EIN and C43LIN shown in DB of FIG. 9 mean each complex with a $GAL4_{DB}$ vector constructed by inserting a gene of wild-type integrase, a D64E mutant gene of integrase and a C43L mutant gene of integrase respectively into MCS (multiple cloning sites) of pPC97 ($GAL4_{DB}$ vector) in accordance with the frame of the $GAL4_{DB}$ vector. In addition, WTIN (gene of wild-type integrase), D64EIN (D64E mutant gene of integrase), C43LIN (C43L mutant gene of integrase), MA (p17 gene contained in a gag domain), CA (p24 gene contained in the gag domain), NC (p7 or p9 gene contained in the gag domain), RT (reverse transferase gene), Vif (viral infectious gene), and Vpr (viral protein r gene) indicated in AD of FIG. 9, mean pPc-86cDNA constructed by inserting DNA being complimentary to each of said genes into MCS of pPC86 ($GAL4_{AD}$ vector). These results indicate that dimer formation ability between integrase molecules is inhibited by C43L mutants.

EXAMPLE 6

Figure 1:
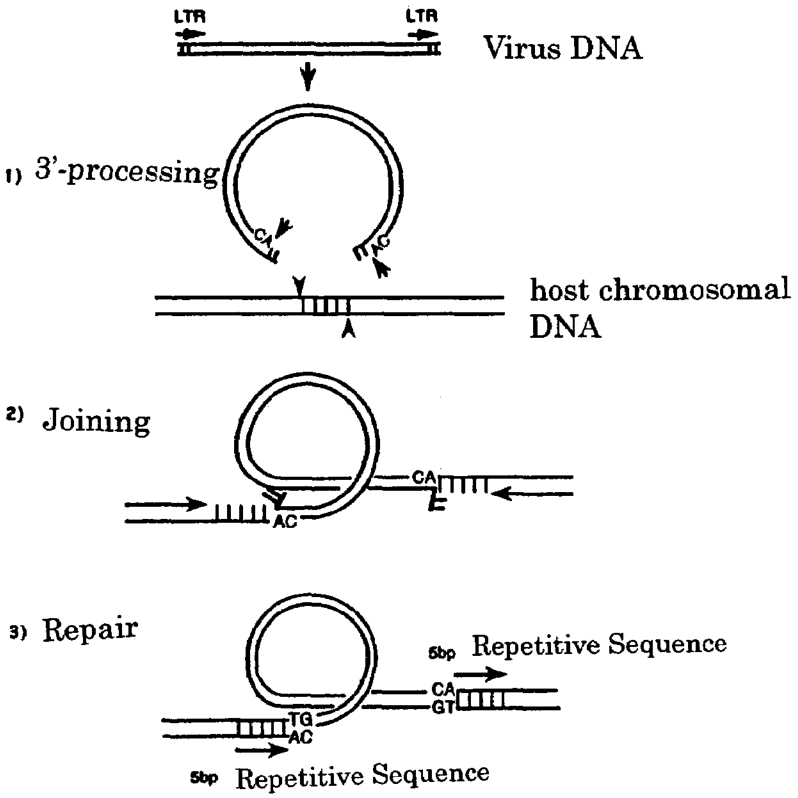
FIG. 1 is a view showing the process of the integration reaction of retroviruses.
Figure 2:
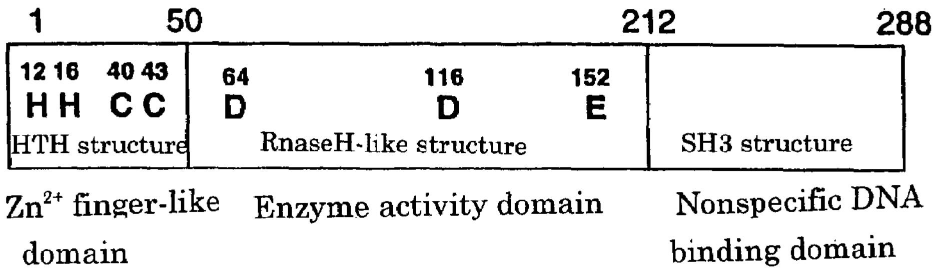
FIG. 2 is a view showing amino acids conserved between retroviral integrases and their positions.
Figure 3:
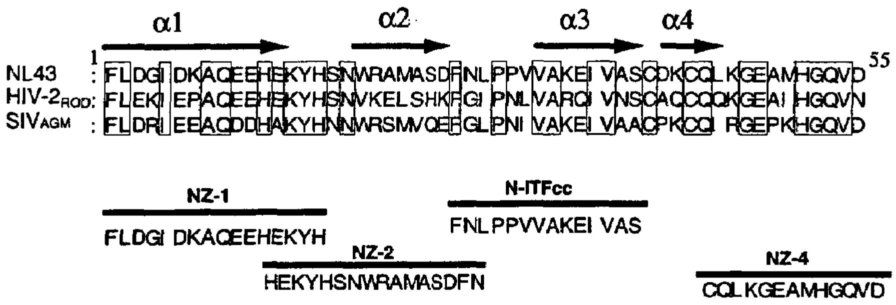
FIG. 3 is a view showing the regions of helix of α1 to α4 in N-terminal domain of HIV-1 integrase (SEQ ID NOS 12-18 are disclosed respectively, in order of appearance).

Inhibitive Activity of a Partial Peptide at N-Terminal Domain of HIV-1 Integrase Chemically synthesized peptides of NZ-1, NZ-2, N-ITFcc and NZ-4 shown in FIG. 3 were diluted with physiological saline to be 20 μM at final concentration, and added to RD cells for 2 hours' treatment. Subsequently, 50 ng NHIV-1 determined by p24 solid phase enzyme immunoassay was inoculated to the treated RD cells to cause a viral infection. Three days after the viral infection, viral genes expressing in the infected cells were measured by the above-stated luciferase assay. In the RD cells treated with the peptides of NZ-1, NZ-2, or NZ-4 showed 10% to 30% suppression, whereas in the RD cells treated with the peptides of NITFcc showed near 80% suppression, indicating that it would be applicable as antiviral drugs.

EXAMPLE 7

Screening of Antiviral Drugs by Phage Display Method with Peptides Binding to N-Terminal Domain of HIV-1 Integrase PCR amplification was conducted with HIV-1 clone (pNL4-3) as a template (the amplification was conducted by 30 cycles; one cycle comprises heat-denaturation at 94° C. for 1 minute, annealing at 60° C. for 1 minute, and synthetic reaction at 72° C. for 2 minutes). DNA fragments at N-terminal domain of HIV-1 integrase (a domain encoding 55 amino acid sequences from N-terminal side) were taken out of the PCR product and inserted into regions such as BamHI or EcoRI in the expression vector pGEX-2T (Pharmacia) to construct the HIV-1 integrase expression vector (pGEX2T-zinc). The constructed vector was introduced into *Escherichia coli* BL21 (DE3). The transformed *Escherichia coli* was added to culture liquid, then IPTG (isopropyl-1-thio-β-D-galactoside) was added to be 100 mM at final concentration, and the expression was induced for 5 hours at 37° C. 5 hours later, the *Escherichia coli* was centrifuged at 3000 rpm for 10 minutes and then collected. Next, *Escherichia coli* collected from medium per 1 L was redissolved in physiological saline containing 100 ml of 1 M NaCl and 3 mM DTT (A solution), and crushed by an ultrasonic treatment (at 500 W for 10 minutes). The obtained solution containing crushed *Escherichia coli* was centrifuged at 12000 rpm for 30 minutes to collect crude fractions of proteins, and integrase N-terminal proteins fused with GST (glutathione-S-transferase) contained in the protein crude fractions were purified by glutathione sepharose beads (Pharmacia).

Next, from phage library (NEB) wherein random peptides with various lengths are inserted into phages, a phage containing a peptide which specifically binds to N-terminal domain of HIV-1 integrase was screened by repeating a panning operation (an operation wherein phage particles which do not bind to GST proteins in each phage library are collected, an operation wherein phage particles which bind to said prepared GST-fused integrase N-terminal protein are collected from selected phages) three to seven times. The obtained phage was cloned and sequenced. It was confirmed by solid phase enzyme immunoassay whether the peptides obtained by phage display method bind to N-terminal domain of HIV-1 integrase as target in vitro (FIG. 10). In detail, a 96-well plate was coated with 100 μg/ml GST-fused integrase N-terminal proteins, GST proteins or nonproteins, and after blocking, cloned phages having each peptide of $10^{11}$ pFU were added to cause a reaction, and then secondary reaction was caused by anti-M13-HRP antibodies (horseradish peroxidase-labeled anti-M13). After the reaction completed, the 96-well plate was made to react with 2,2'-azinobis (3-ethylbenzthiazoline sulfonic acid) (ABTS; Sigma) as a substrate to cause a color reaction, and determined at absorbance of 405 nm. These results have confirmed that each peptide binds to GST-fused integrase N-terminal protein specifically.

INDUSTRIAL APPLICABILITY

The present invention makes it possible to screen a new integrase inhibitor being able to inhibit an HIV infection before the reverse transcription step and having a pharmaceutical site of action totally different from those of traditional integrase inhibitors. Further, it becomes possible to obtain a new integrase inhibitor being able to inhibit the infection and the proliferation of retroviruses completely through the screening. Pharmaceutical constituents containing these new integrase inhibitors are expected as remedies for AIDS.

What is claimed is:

1. A retrovirus comprising a whole or a part of an N-terminal domain of a mutant retroviral integrase, wherein the mutant retroviral integrase comprises a mutation of SEQ ID NO:2 selected from the group consisting of Y15A, wherein the tyrosine at position 15 is substituted with alanine; Y15T, wherein the tyrosine at position 15 is substituted with threonine; P29F, wherein the proline at position 29 is substituted with phenylalanine; V32E, wherein the valine at position 32 is substituted with glutamic acid;

and I36E, wherein the isoleucine at position 36 is substituted with glutamic acid.

2. The retrovirus of claim 1, wherein the mutant integrase is Y15A.

3. The retrovirus of claim 1, wherein the mutant integrase is Y15T.

4. The retrovirus of claim 1, wherein the mutant integrase is P29F.

5. The retrovirus of claim 1, wherein the mutant integrase is V32E.

6. The retrovirus of claim 1, wherein the mutant integrase is I36E.

* * * * *